United States Patent [19]

Fischer

[11] 3,948,914
[45] Apr. 6, 1976

[54] 5-NITROPYRIMIDINE DERIVATIVES

[75] Inventor: Hanspeter Fischer, Bottmingen, Switzerland

[73] Assignee: Ciba-Geigy Corporation, Ardsley, N.Y.

[22] Filed: Nov. 12, 1973

[21] Appl. No.: 415,209

[30] Foreign Application Priority Data
Nov. 16, 1972 Switzerland............... 16728/72

[52] U.S. Cl............... 260/256.4 N; 71/76; 71/92; 260/256.4 C
[51] Int. Cl.[2]............. C07D 239/48; C07D 239/50
[58] Field of Search................. 260/256.4 N

[56] References Cited
UNITED STATES PATENTS

| | | | |
|---|---|---|---|
| 2,557,721 | 6/1951 | Boon et al. | 260/256.4 N |
| 3,159,629 | 12/1964 | Pachter | 260/256.4 N |

OTHER PUBLICATIONS

Goldner et al., Chem. Abstr., Vol. 56, Col. 470f, 1962.
Taylor et al., Chem. Abstr. Vol. 63, Col. 11557d, 1965.
Brown et al., J. Chem. Soc., p. 3770–37708, (1965).

*Primary Examiner*—R. Gallagher
*Assistant Examiner*—James H. Turnipseed
*Attorney, Agent, or Firm*—Harry Falber; Karl F. Jorda

[57] ABSTRACT

Agents and methods of using 4,6-(subst.)diamino-5-nitro-pyrimidines, most of which are new, which possess plant growth inhibiting, in particular herbicidal properties. The agents may also contain salts of the said pyrimidine derivatives. Preferably the 4,6-(subst.)diamino-5-nitro-pyrimidines are also substituted in the 2-position, especially by methyl, ethyl, methoxy or trihalomethyl.

2 Claims, No Drawings

5-NITROPYRIMIDINE DERIVATIVES

The present invention relates to agents which inhibit plant growth, in particular herbicidal agents which contain pyrimidine derivatives as active substances, as well as to new 5-nitropyrimidine derivatives with herbicidal properites. The invention relates also to a process for combating weeds which comprises the use of such active substances and of agents which contain them.

Specific 2,4-bis(substituted amino)-pyrimidines are described in French Pat. No. 1,572,620 as fungicides and insecticides. Dutch Auslegeschrift No. 68,14057 cites substituted pyrimidines which have a fungicidal action chiefly on phytopathogenic fungi on fruit and vegetable plants.

The surprising discovery has now been made that the 5-nitropyrimidines of the formula I, as well as their addition salts, are able to exert an inhibiting effect on the plant metabolism without causing significant damage to emerent plants as a postemergent herbicide.

The active substances of the agents according to the invention have the formula I

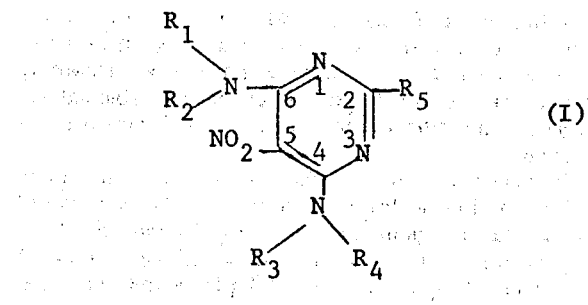

wherein $R_1$ represents an alkyl radical with 1 to 6 carbon atoms, an alkenyl radical with at most 5 carbon atoms, a cycloalkyl, lower alkoxyalkyl, hydroxyalkyl or cyanoalkyl radical, $R_2$ and $R_3$ each independently represents hydrogen or an alkyl radical with 1 to 4 carbon atoms, $R_4$ represents a lower alkyl or cycloalkyl radical, and $R_5$ represents hydrogen or a lower alkoxy, alkyl, haloalkyl, alkylamino or dialkylamino radical or represents a halogen atom.

In formula I, lower alkyl radicals are straight-chain or branched radicals with 1 to 6 carbon atoms, e.g. methyl, ethyl, n-propyl, isopropyl, n-butyl, isobutyl, sec.butyl, tert. butyl, n-pentyl, n-hexyl, and the isomers of the alkyl radicals with 5 and 6 carbon atoms. The lower straight-chain or branched alkyl radicals also form the alkyl moiety of alkoxy, haloalkyl, hydroxalkyl, cyanoalkyl, and alkylamino substituents.

In formula I, alkenyl radicals are straight-chain or branched radicals with 3 to 5 carbon atoms, e.g. propenyl, butenyl, pentenyl radicals; preferred radicals are allyl, methallyl, 3-methyl-butenyl or n-butenyl. As examples of cycloalkyl radicals with 3 to 6 ring carbon atoms there may be mentioned cyclopropyl, cyclobutyl, cyclopentyl, cyclohexyl. These rings can be substituted by methyl or ethyl.

The preferred haloalkyl radical is trifluoromethyl and trichloromethyl. Halogen is to be understood as meaning fluorine, chlorine, bromine, and iodine.

By addition salts are meant the salts with inorganic and organic strong acids, preferably hydrochloric acid, hydrobromic acid, phosphoric acid, sulphuric acid, nitric acid, fluoroboric acid (HBF_4), perchloric acid, methylsulphuric or ethylsulphuric acid, halobenzoic acids, trichloroacetic acid, and aromatic sulphonic acids, such as methanesulphonic acid or p-toluenesulphonic acid.

Preferred compounds are those of the formula I and their salts, wherein $R_1$ represents an alkyl radical with 2 to 6 carbon atoms, a cycloalkyl radical with 3 to 5 carbon atoms, or an alkenyl radical with 3 or 4 carbon atoms, $R_2$ represents hydrogen, $R_3$ represents hydrogen or the methyl group, $R_4$ represents the methyl, ethyl or isopropyl group, and $R_5$ represents the methoxy radical, the methyl or ethyl radical, the trifluoromethyl or trichloromethyl radical, but especially the methyl radical.

Particularly preferred active substances of the formula I are also those in which the substituted amino radicals in 4- and 6-position are not identical and/or at least one of the radicals $R_1$ and $R_4$ is a branched alkyl radical with 3 to 5 carbon atoms.

The active substances contained in the agents according to the invention influence the plant growth in varying manner. Thus first and foremost they inhibit, delay, and prevent germination. As already mentioned, the pyrimidine derivatives of the formula I are not phytotoxic towards the emergent plants when used in the conventional rates of application, but they inhibit the growth in height of individual plant species and also promote bud dormancy. With very high rates of application of over 10 kg of active substance per hectare, the plants can also be damaged in varying degrees and can even die. A number of active substance of the formula I also possess in addition fungicidal, in particular plant-fungicidal, action.

The new agents are particularly suitable for treating cereals and grass crops. In the case of cereals, the growth in height is diminished without any reduction of the crop yield. By treating, for example, emergent summer cereals, rye, oats, and rice (plants in the 2-leaf stage) with 0.5% dispersions of the following active substances:

2-methyl-4-ethylamino-6-(3'-pentyl-amino)-5-nitropyrimidine,
2-methoxy-4,6-bis-ethylamino-5-nitropyrimidine,
2-methyl-4,6-bis(ethylamino)-5-nitropyrimidine,
2-methoxy-4-(3'pentylamino)-5-nitro-6-ethylamino-pyrimidine,
2-methyl-4-(2'-pentylamino)-6-ethylamino-5-nitropyrimidine, there is obtained after 21 days a 50 to 60% inhibition of the growth in height. The plants are sturdy and dark green. Similar results are obtained by treating ornamental plants, e.g. Impatiens spp., Chrysenthemum and soya with 0.1% active substance dispersions. The condition of the test plants is also very good. By treating existing grass crops, the growth in length of the grasses is delayed and the tillering increased. Weeds occurring in meadow grass, e.g. the strongly and rapidly seeding Poa annua, dandelions, plantaginaceae, thistles etc., are very severely inhibited in their germination and emergence and to all intents and purposes aliminated from existing grass crops. The inhibition of the growth in height in a grass mixture consiting of Poa pratensis, Festuca ovina, Festuca rubea and Lolium, is beetween 30 and 70% (rate of application 5 kg/ha).

Further, the active substances, or the corresponding agents, can also be used as growth regulators for decreasing the setting of fruit or for thinning out fruit clusters, for fruit abscission, e.g. of citrus fruit or for delaying blossoming, and also as defoliants and for preventing undesirable formation of side shoots (tobacco, tomatoes, ornamental plants, wines etc.). To be particulary highlighted is the use of the active substances for inhibiting the growth of side shoots in tobacco and suppressing shoots in dormant tubers, for example those of ornamental plants, in potatoes, or in onions. Nitropyrimidines of the formula I when applied in small rates of application impart to the treated plant an increased resistance to drought, frost, and increased salt content in the soil, and increase the sugar content of sugar cane.

First and foremost, however, the new agents can be used as preemergence herbicides in food crops of the most divese kind, such as cereals, maize, rice, cotton, soya, sorghum, sugar beet, potatoes, beans, ground nuts etc. The rates of application vary and depend on the time of application. They are between 0.1 and 10 kg of active substance per hectare in preemergence application and preferably up to 5 kg per hectare for treating existing grass crops, Normally up to 30 kg of active substance is used to prevent the growth of weeds in e.g. railway embackments, factory premises, and roads etc.

HERBICIDAL ACTION IN PREEMERGENCE APPLICATION a. The active substances are mixed with compost earth in concentrations of 32 mg of active substance per liter of earth (=16 kg/ha) and 8 mg of active substance per liter of earth (= 4 kg/ha). The following test plants are sowed in this earth (seed dishes 5 cm deep filled with earth):
Solanum lycopersianum
Setaria italica
Avena sativa
Lolium perenne
Sinapis alba
Stellaria media The seed dishes are then kept at 22°C to 25°C and 50 to 70% relative humidity. The test is evaluated after 20 days. The evaluation is according to the following rating:
1 = plants dead
2–8 = intermediate stages of damage
9 = plants undamaged (control)

b. Immediately after the test plants have been sowed, the active substances are applied as an aqueous suspension, obtained from a 25% wettable powder, to the surface of the earth. The seed dishes are then kept at 22°C to 23°C and 50 to 70% relative humidity. The test is evaluated after 28 days. As test plants there are used:

Weeds

Cyperus esculentus
Lolium multiflorum
Alopecurus myosuorides
Digitaria sanguinalis
Amaranthus docendens
Setaria italica
Echinochloa crus galli
Rottboellia exelt.

Crop plants soya (Glycine hypsida)
cotton (Gossypium herbaccara)
maize (Zea Mais)
wheat (Triticum vulgare)
lucernes (Medicago sativa)
rice (Oryza)
sugar beet
Sorghum hybridum Evaluation is effected according to the rating given under (a). The rates of application are 2 and 4 kg of active substance/ha. In these tests, the agents according to the invention exhibited an excellent herbicidal action on the indicated test weeds. Crop plants are not damaged.

In accordance with method (b) various compounds of the following list were tested. In the subsequent table, the ratings obtained at rates of application of 4 kg/ha stand in front of the comma and those obtained at rates of application of 2 kg/ha stand after the comma.

Lists of active substances of the formula I

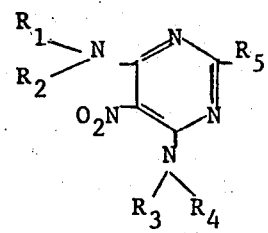

| Compound | $R_1$ | $R_2$ | $R_4$ | $R_3$ | $R_5$ | Physical Data (°C) |
|---|---|---|---|---|---|---|
| 1 | $CH_3$ | H | $CH_3$ | H | $C_2H_5$ | m.p. 169–170° |
| 2 | $i\text{-}C_3H_7$ | H | $i\text{-}C_3H_7$ | H | $C_2H_5$ | m.p. 55–60° |
| 3 | $C_2H_5$ | H | $C_2H_5$ | H | $C_2H_5$ | m.p. 65–68° |
| 4 | $-CH(C_2H_5)_2$ | H | $C_2H_5$ | H | $C_2H_5$ | $n_D^{20} = 1{,}5635$ |
| 5 | $C_2H_5$ | H | $CH_3$ | $CH_3$ | $C_2H_5$ | $n_D^{20} = 1{,}5893$ |
| 6 | $CH_2=CH-CH-$ \| $CH_3$ | H | $C_2H_5$ | H | $C_2H_5$ | |
| 7 | $-CH(CH_3)-C_2H_5$ | H | $C_2H_5$ | H | $C_2H_5$ | $n_D^{20} = 1{,}5640$ |
| 8 | $-CH(CH_3)_2$ | H | $C_2H_5$ | H | $C_2H_5$ | $n_D^{20} = 1{,}5620$ |
| 9 | $C_2H_5$ | $C_2H_5$ | $C_2H_5$ | $C_2H_5$ | $C_2H_5$ | $n_D^{20} = 1{,}5760$ |
| 10 | $-C(CH_3)_3$ | H | $C_2H_5$ | H | $C_2H_5$ | $n_D^{20} = 1{,}5615$ |
| 11 | $CH_3$ | H | $C_2H_5$ | H | $i\text{-}C_3H_7$ | m.p. 50–52° |
| 12 | $i\text{-}C_3H_7$ | H | $i\text{-}C_3H_7$ | H | $i\text{-}C_3H_7$ | m.p. 45° |
| 13 | $C_2H_5$ | H | $C_2H_5$ | H | $i\text{-}C_3H_7$ | m.p. 28° |
| 14 | $-CH(CH_3)-C_3H_7$ | H | $C_2H_5$ | H | $i\text{-}C_3H_7$ | $n_D^{20} = 1{,}5532$ |
| 15 | $CH_3$ | H | $CH_3$ | H | $i\text{-}C_3H_7$ | m.p. 101–102° |
| 16 | $i\text{-}C_3H_7$ | H | $C_2H_5$ | H | $i\text{-}C_3H_7$ | $n_D^{20} = 1{,}5660$ |
| 17 | $-CH(C_2H_5)_2$ | H | $C_2H_5$ | H | $i\text{-}C_3H_7$ | $n_D^{20} = 1{,}555$ |

-continued

| Compound | $R_1$ | $R_2$ | $R_4$ | $R_3$ | $R_5$ | Physical Data (°C) |
|---|---|---|---|---|---|---|
| 18 | —CH—CH$_2$—CH(CH$_3$)$_2$ | H | C$_2$H$_5$ | H | i-C$_3$H$_7$ | $n_D^{20}$ = 1,5558 |
| 19 | C$_2$H$_5$ | H | CH$_3$ | CH$_3$ | i-C$_3$H$_7$ | m.p. 30–31° |
| 20 | —CH(CH$_3$)C$_2$H$_5$ | H | C$_2$H$_5$ | H | CF$_3$ | $n_D^{20}$ = 1,5209 |
| 21 | C$_2$H$_5$ | H | C$_2$H$_5$ | H | CF$_3$ | m.p. 65–70° |
| 22 | i-C$_3$H$_7$ | H | i-(C$_3$H$_7$ | H | CF$_3$ | m.p. 60–65° |
| 23 | —CH(C$_2$H$_5$)$_2$ | H | C$_2$H$_5$ | H | CF$_3$ | $n_D^{20}$ = 1,5175 |
| 24 | CH$_3$ | H | CH$_3$ | H | CF$_3$ | m.p. 140–142° |
| 25 | —CH(CH$_3$)C$_2$H$_5$ | H | C$_2$H$_5$ | H | CCl$_3$ | |
| 26 | i-C$_3$H$_7$ | H | i-C$_3$H$_7$ | H | CCl$_3$ | |
| 27 | —CH(CH$_3$)C$_2$H$_5$ | H | i-C$_3$H$_7$ | H | CCl$_3$ | |
| 28 | Sec.C$_4$H$_9$ | H | CH$_3$ | H | —OCH$_3$ | m.p. 98–99° |
| 29 | i-C$_3$H$_7$ | H | i-C$_3$H$_7$ | H | —OCH$_3$ | m.p. 77–78° |
| 30 | tert.C$_4$H$_9$ | H | C$_2$H$_5$ | H | —OCH$_3$ | m.p. 59–60° |
| 31 | Sec. C$_4$H$_9$ | H | Sec.C$_4$H$_9$ | H | —OCH$_3$ | b.p. 157°/0,001 Torr |
| 32 | C$_2$H$_5$ | H | C$_2$H$_5$ | H | —OCH$_3$ | m.p. 103–105° |
| 33 | —CH(C$_2$H$_5$)$_2$ | H | C$_2$H$_5$ | H | —OCH$_3$ | b.p. 162°/0,001 Torr |
| 34 | Sec. C$_4$H$_9$ | H | C$_2$H$_5$ | H | —OCH$_3$ | b.p. 138°/0,001 Torr |
| 35 | —CH(C$_2$H$_5$)$_2$ | H | —CH(C$_2$H$_5$)$_2$ | H | —OC$_2$H$_5$ | m.p. 45–47° |
| 36 | —CH(C$_2$H$_5$)$_2$ | H | i-C$_3$H$_7$ | H | —OCH$_3$ | b.p. 145°/0,001 Torr |
| 37 | Sec. C$_4$H$_9$ | H | i-C$_3$H$_7$ | H | —OCH$_3$ | b.p. 160°/0,05 Torr |
| 38 | —CH(C$_2$H$_5$)$_2$ | H | i-C$_3$H$_7$ | H | —OC$_2$H$_5$ | b.p. 150°/0,04 Torr |
| 39 | C$_2$H$_5$ | H | C$_2$H$_5$ | H | —OC$_4$H$_9$ | b.p. 185°/0,05 Torr |
| 40 | CH$_3$ | H | CH$_3$ | H | —OCH$_3$ | m.p. 167–168° |
| 41 | i-C$_3$H$_7$ | H | i-C$_3$H$_7$ | H | Cl | m.p. 128–130° |
| 42 | C$_2$H$_5$ | H | C$_2$H$_5$ | H | Cl | m.p. 130–132° |
| 43 | —CH(C$_2$H$_5$)$_2$ | H | i-C$_3$H$_7$ | H | Cl | m.p. 58–60° |
| 44 | n-C$_6$H$_{13}$ | H | n-C$_6$H$_{13}$ | H | —NHC$_6$H$_{13}$(n) | m.p. 58–50° |
| 45 | i-C$_3$H$_7$ | H | i-C$_3$H$_7$ | H | —NH-i-C$_3$H$_7$ | b.p. 185°/0,001 Torr |
| 46 | C$_2$H$_5$ | H | C$_2$H$_5$ | H | —N(CH$_3$)$_2$ | m.p. (crude) 102–105° |
| 47 | —CH(C$_2$H$_5$)$_2$ | H | i-C$_3$H$_7$ | H | —N(CH$_3$)$_2$ | b.p. 160°/0,001 Torr |
| 48 | CH$_3$ | H | CH$_3$ | H | —NHCH$_3$ | m.p. 155–157° |
| 49 | Sec. C$_4$H$_9$ | H | Sec. C$_4$H$_9$ | H | H | b.p. 104°/0,001 Torr |
| 50 | C$_2$H$_5$ | H | C$_2$H$_5$ | H | H | m.p. 80–81° |
| 51 | —CH(C$_2$H$_5$)$_2$ | H | CH$_3$ | CH$_3$ | H | b.p. 120°/0,001 Torr |
| 52 | —CH(C$_2$H$_5$)$_2$ | H | i-C$_3$H$_7$ | H | H | |
| 53 | tert. C$_4$H$_9$ | H | tert. C$_4$H$_9$ | H | H | m.p. 106–107° |
| 54 | CH$_3$ | CH$_3$ | CH$_3$ | H | H | m.p. 96–97° |
| 55 | CH$_3$ | H | CH$_3$ | H | H | m.p. 192–193° |
| 56 | —CH(C$_2$H$_5$)$_2$ | H | C$_2$H$_5$ | H | H | |
| 57 | —CH(CH$_3$)C$_2$H$_5$ | H | C$_2$H$_5$ | H | H | |
| 58 | CH$_2$=CH—CH$_2$— | H | CH$_2$=CH—CH$_2$— | H | CH$_3$ | m.p. 70–72° |
| 59 | cyclopropyl | H | cyclopropyl | H | CH$_3$ | m.p. 147–148° |
| 60 | i-C$_3$H$_7$ | H | iC$_3$H$_7$ | H | CH$_3$ | m.p. 99–101° |
| 61 | Sec. C$_4$H$_9$ | H | Sec. C$_4$H$_9$ | H | CH$_3$ | m.p. 36–39° |
| 62 | —CH(C$_2$H$_5$)$_2$ | H | C$_2$H$_5$ | H | CH$_3$ | b.p. 140°/0,001 Torr |
| 63 | —CH(C$_2$H$_5$)$_2$ | H | i-C$_3$H$_7$ | H | CH$_3$ | b.p. 100°/0,02 Torr |
| 64 | n-C$_6$H$_{13}$ | H | n-C$_6$H$_{13}$ | H | CH$_3$ | m.p. 41–43° |
| 65 | C$_2$H$_5$ | H | C$_2$H$_5$ | H | CH$_3$ | m.p. 109–111° |
| 66 | C$_2$H$_5$ | C$_2$H$_5$ | C$_2$H$_5$ | C$_2$H$_5$ | CH$_3$ | m.p. 58–60° |
| 67 | cyclopentyl | H | cyclopentyl | H | CH$_3$ | m.p. 71–73° |
| 68 | —C(CH$_3$)$_2$CN | H | C$_2$H$_5$ | H | CH$_3$ | m.p. 76–78° |
| 69 | —CH$_2$—CH$_2$—OH | H | C$_2$H$_5$ | H | CH$_3$ | m.p. 128–130° |
| 70 | —CH$_2$—CH$_2$—OCH$_3$ | H | C$_2$H$_5$ | H | CH$_3$ | m.p. 64–66° |
| 71 | CH$_2$=CH—CH$_2$— | H | C$_2$H$_5$ | H | CH$_3$ | m.p. 77–79° |
| 72 | cyclopropyl | H | C$_2$H$_5$ | H | CH$_3$ | m.p. 118–119° |
| 73 | —CH(CH$_3$)C$_2$H$_5$ | H | i-C$_3$H$_7$ | H | CH$_3$ | m.p. 40–42° |
| 74 | n-C$_4$H$_9$ | H | n-C$_4$H$_9$ | H | CH$_3$ | m.p. 60–62° |
| 75 | cyclohexyl | H | C$_2$H$_5$ | H | CH$_3$ | m.p. 78–80° |
| 76 | C$_2$H$_5$ | H | CH$_3$ | CH$_3$ | CH$_3$ | m.p. 98–99° |
| 77 | C$_4$H$_9$ | C$_4$H$_9$ | C$_4$H$_9$ | C$_4$H$_9$ | CH$_3$ | b.p. 180°/0,001 Torr |
| 78 | CH$_3$ | H | CH$_3$ | H | CH$_3$ | m.p. 200–201 |
| 79 | —CH(CH$_3$)—CH$_2$—OCH$_3$ | H | C$_2$H$_5$ | H | CH$_3$ | |
| 80 | —CH(CH$_3$)C$_3$H$_7$ | H | i-C$_3$H$_7$ | H | CH$_3$ | $n_{20}^D$ = 1,5590 |

The following Table I gives some results according to test method a): Table I

| Compound | Concentration kg/ha | Solanum | Setaria | Avena sat. | Lolium | Sinapis | Stellaria |
|---|---|---|---|---|---|---|---|
| 28 | 16 | 2 | 1 | 7 | 3 | 8 | 6 |

-continued

| Compound | Concentration kg/ha | Solanum | Setaria | Avena sat. | Lolium | Sinapis | Stellaria |
|---|---|---|---|---|---|---|---|
| 33 | 16 | 2 | 1 | 3 | 1 | 3 | 1 |
| 36 | 16 | 2 | 1 | 3 | 2 | 5 | 1 |
| 43 | 16 | 7 | 1 | 6 | 1 | 8 | 9 |
| 49 | 16 | 4 | 2 | 6 | 3 | 7 | 6 |
| 62 | 16 / 4 |  | 1 | 1 / 2 |  | 2 / 4 | 2 |

A number of results according to test method (b) are listed in the following Table 2: (ratings for 4 kg/ha before the comma, ratings for 2 kg/ha after the comma.

Table II

| | Crop plants | | | | | | | | |
|---|---|---|---|---|---|---|---|---|---|
| Compound | Beta Sugar Beet | Cotton | Soya Glycine | Water Rice Oryza | Dry Rice Oryza | Sorghum hybridum | Maize Zea | Wheat Triticum | Luzernes Medicago |
| 13 | 6,7 | 9,9 | 9,9 |  | 6,8 | 6,7 | 6,6 | 8,8 | 9,9 |
| 33 | 4,9 | 7,9 | 7,8 | 1,1 | 2,7 | 8,8 | 9,9 | 7,9 | 8,9 |
| 36 | 6,7 | 9,9 | 7,9 | 1,2 | 3,8 | 2,2 | 3,7 | 9,9 | 9,9 |
| 38 | 9,9 | 9,9 | 9,9 |  | 6,6 | 4,7 | 8,8 | 5,7 | 9,9 |
| 43 | 9,9 | 9,9 | 2,9 | 3,4 | 6,7 | 8,8 | 9,9 | 9,9 | 9,9 |
| 47 | 8,9 | 9,9 | 9,9 |  | 4,5 | 9,9 | 9,9 | 9,9 | 8,9 |
| 58 | 8,9 | 9,9 | 9,9 |  | 2,6 | 6,9 | 8,9 | 7,8 | 7,8 |
| 59 | 7,9 | 9,9 | 9,9 |  | 6,6 | 8,8 | 8,9 | 3,8 | 7,9 |
| 62 | 2,2 | 7,9 | 9,9 |  | 3,3 | 2,6 | 7,8 | 5,6 | 5,6 |
| 63 | 3,7 | 7,8 | 9,9 |  | 7,7 | 1,2 | 3,6 | 2,3 | 6,8 |

| | Weeds | | | | | | | |
|---|---|---|---|---|---|---|---|---|
| Compound | Cyperus esculentus | Lolium multiflorum | Alopecurus myos. | Digitaria sanguin. | Amaranthus | Setaria italica | Echinochloa crusgalli | Rottboellia exelt. |
| 13 | 1 | 8,8 | 7,7 | 1,3 | 3,4 | 2,6 | 2,3 | 4,5 |
| 33 | 9 | 2,3 | 2,2 | 1,1 | 1,1 | 1,1 | 1,1 | 1,1 |
| 36 | 9 | 1,2 | 1,1 | 1,1 | 2,2 | 1,1 | 1,1 | 1,1 |
| 38 |  | 3,3 | 2,3 | 2,2 | 3,4 | 1,2 | 1,1 | 2,2 |
| 43 |  | 3,5 | 2,3 | 1,3 | 2,2 | 7,7 | 1,2 | 6,7 |
| 47 |  | 3,3 | 2,2 | 2,3 | 5,9 | 4,7 | 2,2 | 6,8 |
| 58 | 8 | 2,6 | 2,8 | 1,1 | 3,4 | 4,5 | 1,2 | 2,4 |
| 59 |  | 7,8 | 7,8 | 2,2 | 3,4 | 2,8 | 2,3 | 6,6 |
| 62 | 8 | 1,2 | 1,1 | 1,1 | 1,1 | 1,1 | 1,1 | 2,2 |
| 63 | 7 | 1,2 | 1,1 | 1,1 | 1,2 | 1,1 | 1,1 | 2,2 |

Agents containing the following active substances exhibited particularly good herbicidal properties:
2-chloro-4-isopropylamino-6-pentyl-(3)-amino-5-nitro-pyrimidine
2-chloro-4,6-bis-isopropylamino-5-nitro-pyrimidine
2-methoxy-4,6-bis-ethylamino-5-nitro-pyrimidine
2-methoxy-4-sec.butylamino-6-methylamino-5-nitropyrimidine
2-methoxy-4-ethylamino-6-tert.butylamino-5-nitropyrimidine
2-methoxy-4,6-bis-isopropylamino-5-nitro-pyrimidine
2-methoxy-4-sec.butylamino-6-ethylamino-5-nitropyrimidine
2-methoxy-4-pentyl-(3)-amino-6-ethylamino-5-nitropyrimidine
2-methyl-4-pentyl(3)-amino-6-ethylamino-5-nitropyrimidine
2-methoxy-4-isopropylamino-6-pentyl-(3)-amino-5-nitro-pyrimidine
2-dimethylamino-4-isopropylamino-6-pentyl-(3)-amino-5-nitropyrimidine
2-ethylamino-4-isopropylamino-6-pentyl-(3)-amino-5-nitropyrimidine and the corresponding 2-isopropyl-pyrimidines and 2-trifluoromethyl-pyrimidines.

The agents according to the invention are manufactured in known manner by intimately mixing and/or grinding active substances of the formula I with the suitable carriers, optionally with the addition of dispersants or solvents which are inert towards the active substances. The active substances may take and be used in the following forms:

Solid forms: dusts, tracking agents, granules, coated granules, impregnated granules and homogeneous granules.

Liquid forms: (a) active substances which are dispersible in water: wettable powders, pastes, emulsions; (b) solutions.

To manufacture solide forms (dusts, tracking agents), the active substances are mixed with solid carriers. Suitable carriers are, for example: kaolin, talcum, bolus, loess, chalk, limestone, ground limestone, attaclay, dolomite, diatomacous earth, precipitated silica, alkaline earth silicates, sodium and potassium aluminium silicates (feldspar and mica), calcium and magnesium sulphates, magnesium oxide, ground synthetic materials, fertilisers, for example ammonium sulphate, ammonium phosphate, ammonium nitrate, urea, ground vegetable products, such as corn meal, bark dust, sawdust, nutshell meal, cellulose powder, residues of plant extractions, activated charcoal etc. These substances can either be used singly or in admixture with one another.

The particle size of the carriers for dusts is advantageously up to 0.1 mm, for tracking agents from about 0.075 to 0.2 mm, and for granules 0.2 mm or larger.

The solid forms contain the active substances in concentrations from 0.5% to 80%.

To these mixtures can also be added additives which stabilize the active substance and/or non-ionic, anionic and cationic surface active substances, which for example improve the adhesion of the active ingredients on plants or parts of plants (adhesives and agglutinants) and/or ensure a better wettability (wetting agents) and dispersibility (dispersing agents). Examples of suitable adhesives are the following: olein/chalk mixture, cellulose derivatives (methyl cellulose, carboxymethyl cellulose), hydroxyethyl glycol ethers of monoalkyl and dialkyl phenols having 5 to 15 ethylene oxide radicals per molecule and 8 to 9 carbon atoms in the alkyl radical, lignin sulphonic acids, their alkali metal and alkaline earth metal salts, polyethylene glycol ethers (carbowaxes), fatty alcohol polyethylene glycol ethers having 5 to 20 ethylene oxide radicals per molecule and 8 to 18 carbon atoms in the fatty alcohol moiety, condensation products of urea and formaldehyde, and also latex products.

The water-dispersible concentrates of the active substance i.e., wettable powders, pastes and emulsifiable concentrates, are agents which can be diluted with water to any concentration desired. They consist of active substance, carrier, optionally additives which stabilize the active substance, surface-active substances and anti-foam agents and, optionally, solvents. The active substance concentrations in these agents are from 5 – 80%.

Wettable powder and pastes are obtained by mixing and grinding the active substances with dispersing agents and pulverulent carriers in suitable apparatus until homogeneity is attained. Carriers are, for example, those mentioned for the solid forms of application. In some cases it is advantageous to use mixtures of different carriers. As dispersing agents there can be used, for example, condensation products of sulphonated naphthalene and sulphonated naphthalene derivatives with formaldehyde, condensation products of naphthalene or naphthalene sulphonic acids with phenol and formaldehyde, as well as alkali, ammonium and alkaline earth metal salts of lignin sulphonic acid, in addition, alkylaryl sulphonates, alkali and alkaline earth metal salts of dibutyl naphthalene sulphonic acid, fatty alcohol sulphates such as salts of sulphated hexadecanols, heptadecanols, octadecanols, and salts of sulphated fatty alcohol glycol ethers, the sodium salt of oleoyl, the sodium salt of olcoyl methyl tauride, ditertiary acetaline glycols, dialkyl dilauryl ammonium chloride and fatty acid alkali and alkaline earth metal salts. Suitable anti-form agents are silicones.

The active substance is so mixed, ground sieved and strained with the additives mentioned above that, in wettable powders, the solid particle size of 0.02 to 0.04 mm and in pastes, of 0.03 mm is not exceeded. To procuede emulsifiable concentrates and pastes, dispersing agents such as those given in the previous paragraphs, organic solvents and water are used. Examples of suitable solvents are the following alcohols, benzene, xylenes, toluene, dimethyl sulphoxide, and mineral oil fractions boiling between 120° and 350°C. The solvents must be practically odorless, not phytotoxic, inert to the active substances and not readily inflammable.

Furthermore, the agents according to the invention can be applied in the form of solutions. For this purpose the active substances or several active substances of general formula II are dissolved in suitable organic solvents, mixtures of solvents or in water. Aliphatic and aromatic hydrocarbons, chlorinated derivatives thereof, alkyl naphthalenes and mineral oils singly or in admixture, can be used as organic solvents. The solutions contain the active substance in a concentration range from 1% to 20%. These solutions can be applied either with a propellant gas (as spray) or with special sprays (as aerosol). The agents described according to the invention can be mixed with other biocidally active substances or agents. Thus in order to broaden the activity spectrum the new agents may contain, for example, insecticides, fungicides, bactericides, fungistatics, bacteriostatics or nematocides, in addition to the cited active substance of the formula I. The agents according to the invention may also contain plant fertilisers, trace elements etc.

Granules

The following substances are used to produce 5% granules:

5 parts of active substance,
0.25 parts of epichlorohydrin,
0.25 parts of cetyl polyglycol ether,
3.50 parts of polyethylene glycol,
91 parts of kaolin (particle size 0.3 – 0.8 mm).

The active substance is mixed with epichlorophydrin and dissolved with 6 parts of acetone; the polyethylene glycol and cetyl polyglycol ether are then added. The thus obtained solution is sprayed on kaolin, and the acetone subsequently evaporated in vacuo.

Wettable Powder

The following constituents are used to manufacture (a) a 50%, (b) a 25% and (c) a 10% wettable powder:

a.

50 parts of 2-methoxy-4-ethylamino-5-nitro-6-(pent-3'-ylamino)-pyrimidine
5 parts of sodium dibutylnaphthalene sulphonate,
3 parts of naphthalenesulphonic acid/phenolsulphonic acid/formaldehyde condensate (3:2:1),
20 parts of kaolin,
22 parts of Champagne chalk;

b.

25 parts of 2-methyl-4-isopropylamino-5-nitro-6-methylamino-pyrimidine
5 parts of sodium oleylmethyltauride,
2.5 parts of naphthalenesulphonic acid/formaldehyde condensate,
0.5 part of carboxymethyl cellulose,
5 parts of neutral potassium aluminium silicate,
62 parts of kaolin;

c.

10 parts of 2-dimethylamino-4-sec. butylamino-5-nitro-6-methylamino-pyrimidine,
3 parts of a mixture of the sodium salts of saturated fatty alcohol sulphates,
5 parts of napthalenesulphonic acid/formaldehyde condensate.
82 parts of kaolin.

The indicated active substance is applied to the corresponding carriers (kaolin and chalk) and then these are mixed and ground, to yield wettable powders of excellent wettability and having an excellent capacity for forming suspensions. By diluting these wettable powders with water it is possible to obtain suspensions of every desired concentration of active substance. Such suspensions are used for combating weeds and grass-like weeds in food crops in the preemergence method and for treating grass crops.

Paste

The following substances are used to manufacture a 45% paste:
45 parts of 2-chloro-4-isopropylamino-5-nitro- 6-(pent-3'-yl-amino)-pyrimidine,
5 parts of sodium aluminium silicate,
14 parts of cetyl polyglycol ether with 8 mols of ethylene oxide.
1 part of oleyl polyglycol ether with 5 mols of ethylene oxide,
2 parts of spindle oil,
10 parts of polyethylene glycol,
23 parts of water.

The active substance is intimately mixed with the addition in appropriate devices and ground. A paste is obtained from which, by diluting it with water, is possible to manufacture suspensions of every desired conentration of active substance. The suspensions are suitable for treating rose gardens.

Emulsions Concentrate

To manufacture a 25% emulsion concentrate
25 parts of 2-methyl-4-isopropylamino-5-nitro-6-pentyl(3)-amino-pyrimidine,
5 parts of a mixture of nonylphenolpolyoxy-ethoxyethylene and calcium, dodecylenesulphonate,
35 parts of 3,5,5-trimethyl-2-cyclohexan-1-one,
35 parts of dimethyl formamide, are mixed together. This concentrate can be diluted with water to give emulsions in desired concentrations. Such emulsions are suitable for combating weeds in food crops.

Instead of the respective acrive substance used in the preceding formulations, it is also possible to use another of the compounds comprised by the formula I.

The majority of the active substances of the formula I and of the substances contained in the preceding list are new compounds which have not yet been described in the literature.

Only a number of compounds are known, for example those in which $R_5$ represents hydrogen or methyl and $R_2$ and $R_3$ together represent hydrogen and $R_1$ and $R_4$ represent similar lower alkyl radicals (methyl, tert. butyl) [J. Chem. Soc. 1970, p. 494; 1965, p. 3770 and J. Appl. Chem. 74 (1954)].

Particularly active new compounds are those which have the formula I$a$

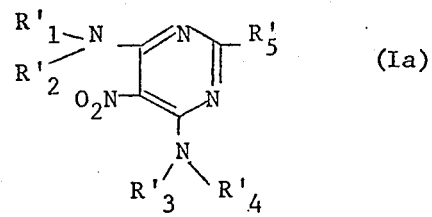

wherein $R'_1$ represents an alkyl radical with 1 to 6 carbon atoms, an alkenyl radical with at most 5 carbon atoms, a cycloalkyl radical, or a lower hydroxyalkyl or a cyanoalkyl radical, $R'_2$ and $R'_3$ each represents hydrogen or lower alkyl, $R'_4$ represents an alkyl radical with 2 to 6 carbon atoms or represents a cycloalkyl radical, and $R'_5$ represents the methoxy radical, an alkyl radical with 1 to 4 carbon atoms, the dimethylamino radical or a trihalomethyl radical.

Among these compounds, particular prominence in respect of their action attaches to those in which $R'_5$ represents lower alkyl, especially methyl, $R'_1$ and $R'_4$ represents cycloalkyl or alkyl radicals, at least one of which is branched, and the substituted amino radicals in 4- and 6-position are not identical.

The new active substances of the formulae I and I$a$ are manufactured by methods corresponding to those proposed for the manufacture of the known representatives of this group of compounds.

The new 5-nitropyrimidines of the formula I$a$ are obtained according to the present invention by reacting a corresponding 4,6-dihalo-5-nitropyrimidine derivative of the formula II

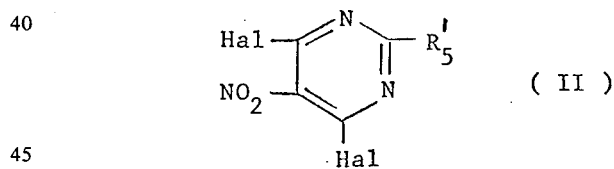

wherein $R'_5$ has the meanings indicated under formula I$a$ and Hal represents in each case a halogen atom, preferably chlorine or bromine, successively with amines of the formulae III and/or IV

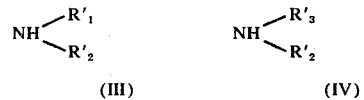

in the presence of an acid acceptor and optionally of a solvent and/or diluent. In the formulae II, III, and IV, the symbols $R'_1$ to $R'_5$ have the meanings indicated under the formula I$a$.

The necessary stepwise exchange when using different amines of the formula III or IV is dependent both on temperature as well as on time and solvent. In general, the reaction temperatures are in the range from −60°C to +120°C; for the exchange of the first halogen atom it is necessary to choose temperatures between −60°C to +120°C and for the exchange of the second halogen atom between 10°C and 50°C or higher.

Suitable solvents for the reactions according to the invention are water, ketones, such as acetone or methyl ethyl ketone, ethers and ethereal compounds, such as dioxan or tetrahydrofuran, aliphatic and aromatic hydrocarbons and halogenated hydrocarbons, also nitriles, such as acetonitrile, N,N-dialkylated amides, such as dimethyl formamide, or sulphoxides, such as dimethyl sulphoxide, as well as mixtures of such solvents.

The most suitable acid acceptors for the process according to the invention are inorganic bases, such as hydroxides, hydrogen carbonates and carbonates of alkali metals and alkaline earth metals. But tertiary amines, such as trialkylamines, dialkylamines, pyridine, and pyridine bases, are also possible as organic bases. It is also possible to use as acid acceptor the respective amino component of the formula III or IV in excess. Sodium hydroxide or potassium hydroxide are preferred.

After substitution of the radical of an amine of the formula III or IV for a halogen atom, it is possible to isolate 4(6)-amino-6-(4)-halo-5-nitropyrimidine derivatives as intermediates, some of which have not yet been described in the literature.

For the manufacture of 4,6-diamino-5-nitro-pyrimidine derivatives of the formula Ia, in which $R'_5$ represents a dimethylamino group or the methoxy radical, there is used as starting material either 2,4,6-trihalo-5-nitropyrimidine or a 2-alkylthio-4,6-dichloro-5-nitropyrimidine derivative. The halogen atoms in 4- and 6-position are replaced in the manner described hereinbefore and the remaining halogen atom in 2-position is then replaced by the radical of the corresponding amine or alcohol.

The reaction temperature for this process step are from 30°C to 120°C. Suitable acid acceptors and suitable solvents or diluents are those cited hereinbefore.

The desired 4,6-diamino-5-nitro-2-alkoxy-pyrimidines are obtained by substituting the radical RO for the RS group of a 2-alkylthio-4,6-diamino-pyrimidine using an alkanolate, for example an alkali metal methylate, in the presence of a solvent or diluent, preferably of the alkanol corresponding to the alkanolate, or also of dimethyl sulphoxide, dimethyl cellosolve etc., at temperatures between 0°C and 130°C.

Addition salts are manufactured by reacting the pyrimidine derivatives of the formulae I and Ia in known manner with inorganic and organic acids. The strong acids, e.g. hydrohalic acids, sulphuric acid, fluoroboric acid, phosphoric acid, alkylsulphuric acid, are preferred for the pyrimidine derivatives of the formula I.

The following Examples will serve to illustrate the process for the manufacture of the described compounds. These and other pyrimidine derivatives of the formulae I and Ia manufactured by the methods described in the Examples have already been listed in the opening portion of the description.

EXAMPLE 1 a. 50 g of ethylamine gas are slowly passed into a solution of 60.0 g of 2-methylthio-4,6-dichloro-5-nitro-pyrimidine in 750 ml of absolute ethanol at about 35°C and without cooling. The mixture is subsequently stirred for 2 hours at room temperature and concentrated to dryness in vacuo at 45°C. The residue is suspended in 500 ml of water, isolated, and washed with water. The product is recrystallised from a mixture of hexane and pentane in the ratio 10:1. The 2-methylthio-4,6-bis-ethylamino-5-nitro-pyrimidine has a melting point of 130°–131°C.

b. 11.25 g of 4,6-diethylamino-2-methylthio-5-nitropyrimidine are added to 200 ml of absolute methanol. Then 20 ml of triethylamine and subsequently a solution of 3.2 g of sodium methylate in 50 ml of absolute methanol are added. This mixture is stirred for 20 hours at 90°C under reflux, then cooled to room temperature. The solution is then poured into 2 liters of ice water and the temperature is kept at 25°C with a little ice. The precipitated crystals are filtered off with suction, washed with water, and dried in a water jet vacuum at 70°C over KOH for 16 hours. Yield: 9.3 g of 2-methoxy-4,6-bis-ethylamino-5-nitro-pyrimidine with a melting point of 98°–100°C. Recrystallisation from isopropyl ether yields yellow crystals with a melting point of 103°–105°C.

EXAMPLE 2

At 0°C, 3 g of ethylamine gas are passed into a solution of 3.7 g of 2,4,6-trichloro-5-nitro-pyrimidine and 50 ml of ethanol. The solution is then kept for 30 minutes at 5° to 10°C and subsequently evaporated to dryness in vacuo at 30°C. The residue is washed with water and dried. The 2-chloro-4,6-bis-ethylamino-5-nitro-pyrimidine has a melting point of 130°–132°C. 2-methoxy-4,6-bis-ethylamino-5-nitro-pyrimidine according to Example 1b is obtained by heating a solution of 2-chloro-4,6-bis-ethylamino-5-nitro-pyrimidine in methanol in the presence of sodium methylate.

EXAMPLE 3

30 g (0.1 mol) of 2-methyl-mercapto-4-ethylamino-5-nitro-6-(3-pentyl-amino)-pyrimidine are dissolved in 400 ml of methanol. A solution of 8.1 g (0.15 mol) of sodium methylate in 100 ml of methanol is added together with 20 ml of triethylamine to the previously prepared solution. The mixture is refluxed for 16 hours, evaporated, and the residue is treated with 200 ml of water. After extracting 3 times with ether, the extracts are dried over $MgSO_4$, dried, filtered, and the ethereal solution is evaporated, to leave as residue 21.1 g of 2-methyoxy-4-ethylamino-5-nitro-6-(3-pentylamino)-pyrimidine with a boiling point of 162°C/0.001 Torr (74.5% of theory).

|  | C | H | N | S |
|---|---|---|---|---|
| Analysis: calc. | 50,87 | 7,47 | 24,72 | — |
| found | 51,53 | 7,66 | 24,45 | <0.3 |

EXAMPLE 4

20.7 g of 2-methyl-4,6-dichloro-5-nitro-pyrimidine are dissolved in 300 ml of alcohol and then 12 ml of triethylamine are added. Subsequently 6 g of ethylamine are passed in or added dropwise at 25°–30°C in an ice bath. The reaction mixture is stirred for ½ hour at room temperature, then evaporated, and the residue is treated with 300 ml of water. The precipitate is filtered off with suction and the filter residue is washed with water until the runnings contain no more chlorine ions. The product is then dried in a water jet vacuum at 50°C. to yield 2-methyl-4,6-bis-ethyl-amino-5-nitro-pyrimidine with a melting point of 109°–110°C.

EXAMPLE 5 a. 30 ml of triethylamine are added to 32.5 g (0.156 mol) of 2-methyl- 4,6-dichloro-5-nitro-pyrimidine. At −18°C, 3.5 g of isopropylamine (0.16 mol) are added dropwise and the mixture is then stirred for 1 ¼ hours at this temperature. The mixture is subsequently poured on 4 liters of water, the precipitate is filtered off with suction, and washed 3 times with water. The crude product is dried at 50°C and 11 Torr for 16 hours, to yield 26.4 g of 2-methyl-4-chloro-5-nitro-isopropylamino-pyrimidine with a melting point of 69°–72°C. The pure substance (recrystallised from hexane) melts at 77°–79°C.

b. 10 ml of triethylamine are added to 8.05 g (0.035 mol) of 2-methyl-4-chloro-5-nitro-6-isopropylamino-pyrimidine. While cooling with ice, 7.3 g (0.1 mol) of sec- butylamine are slowly added dropwise and the mixture is stirred for 16 hours at room temperature. The reaction solution is evaporated, the residue suspended in 500 ml of water and extracted 3 times with ether, to yield 9.0 g of 2-methyl-4-isopropylamino-6-sec.butylamino-5-nitro-pyrimidine (36.5%) as an oil.

EXAMPLE 6

5 ml of triethylamine are added to a solution of 5.4 g (0.025 mol) of 2-methyl-4-ethylamino-5-nitro-6-chloropyrimidine (m.p. 58°–61°C and manufactured in a manner analogous to that of Example 5a) in 150 ml of absolute alcohol and then 2.6 g (0.03 mol) of 3-aminopentane are added. The mixture is evaporated after 2 hours, the residue is treated with about 300 ml of water, and extracted twice with ether. The combined ethereal extracts are dried with $MgSO_4$, filtered and evaporated, to yield 7.5 g of 2-methyl-4-ethylamino-5-nitro-6-(3'-pentylamino)-pyrimidine with a boiling point of 140°C/0.001 Torr.

|  | C | H | N | Cl |
|---|---|---|---|---|
| Analysis: calc. | 53,91 | 7,92 | 26,20 | — |
| found | 53,86 | 7,95 | 25,83 | <0,1 |

EXAMPLE 7

19.4 g (0.1 mol) of 4,6-dichloro-5-nitro-pyrimidine are dissolved in 250 ml of alcohol and subsequently 22.5 g of ethylamine (0.5 mol) are passed into this solution at a maximum temperature of 40°C (ice bath). The mixture is stirred for 15 minutes, then evaporated, and the residue is treated with water. The suspension is filtered with suction and washed 3 times with water. After drying for 16 hours at 50°C and 11 Torr there are obtained 19.9 g of 4,6-bis(ethylamino)-5-nitro-pyrimidine (m.p. 80°–81°C); m.p. 81°–82°C after recrystallisation from hexane.

|  | C | H | N | Cl |
|---|---|---|---|---|
| Analysis: calc. | 45,09 | 6,20 | 33,15 | — |
| found | 45,57 | 6,11 | 33,03 | <0,1 |

EXAMPLE 8

5.4 g of 4-isopropylamino-5-nitro-6-chloro-pyrimidine (J. Chem. Soc. 1970/494) (0.025 mol) are dissolved in alcohol and the solution is treated with 5 ml of triethylamine. 3.5 g (0.04 mol) of pentyl-(3)-amine are added at room temperature and the mixture is subsequently refluxed for 16 hours at about 100°C bath temperature. The mixture is evaporated, the residue treated with about 200 ml of water and extracted 3 times with ether. These ethereal extracts are dried over $MgSO_4$ and evaporated. The residue contains the desired 4-isopropylamino-5-nitro-6-(3-pentylamino)-pyrimidine.

EXAMPLE 9

15.6 g of 2-methylmercapto-4-isopropylamino-5-nitro-6-(3-pentyl-amino)-pyrimidine (0.05 mol) are dissolved in 250 ml of alcohol. Then 20 ml of triethylamine and 3 g of dimethylamine are added. The reaction mixture is kept for 16 hours under high pressure (12 bar) at 100°C, until no more starting material can be detected in a thin-layer chromatogram (silica gel. hexane/acetone 5:1). The mixture is evaporated, the residue is treated with water and extracted twice with ether. The ethereal extracts are dried over $MgSO_4$, filtered and evaporated, to yield 13.5 g of 2-dimethylamino-4-isopropyl-amino-5-nitro-6-(3-pentylamino)-pyrimidine; b.p. 160°C/0.001 Torr.

|  | C | H | N | Cl |
|---|---|---|---|---|
| Analysis: calc. | 54,17 | 8,44 | 27,08 | — |
| found | 55,06 | 8,54 | 26,55 | <0,5 |

EXAMPLE 10

1.15 g (0.005 mol) of 2,4,6-trichloro-5-nitropyrimidine are dissolved in 50 ml of alcohol and the solution is then treated with 2.9 g (0.05 mol) of isopropylamine. The mixture is stirred for 3 hours at room temperature after the temperature has first risen to 35°C, and then it is evaporated. The residue is treated with 100 ml of water and extracted twice with ether. The ethereal extract is dried over $MgSO_4$ for 4 hours, filtered, and evaporated, to yield 1.1 g of 2,4,6-tri-isopropylamino-5-nitro- pyrimidine as an oil; b.p. 185°C at 0.001 Torr.

EXAMPLE 11 a. 10 mols of isobutyronitrile and 10 mols of abs. ethanol are mixed and 10 mols of HCl gas are passed in at a maximum temperature of 30°C. After the mixture has been stirred overnight, a solution of 10 mols of ammonia in 1.5 liters of abs. ethanol is added dropwise and the batch is stirred overnight. The reaction solution is filtered and concentrated to dryness. The residue is dissolved in about 2 liters of methanol and this solution is added to a solution of 30 mol of $NaOCH_3$ in 3.5 liters of methanol. After the addition, the mixture is stirred overnight. The reaction mixture is subsequently concentrated, the residue taken up in water and acidified with HCl, whereupon 4,6-dihydroxy-2-isopropyl-pyrimidine crystallises out; m.p. 290°C–300°C.

b. 220 g of 4,6-dihydroxy-2-isopropyl-pyrimidine are added at 0°C to 500 ml of 100% nitric acid and the mixture is stirred for 1 hour. Subsequently the nitration mixture is poured on ice water, filtered, washed with water, and dried in vacuo over $P_2O_5$, to yield 110 g of 4,6-dihydroxy-2-isopropyl-5-nitro-pyrimidine; mp. 300°C.

c. 110 g (0.55 mol) of 4,6-dihydroxy-2-isopropyl-5-nitro-pyrimidine are added to 400 ml of $POCl_3$. Then 110 ml of N,N-diethyl aniline are added dropwise, whereupon the temperature rises to 45°C. The mixture is refluxed for 1 hour and, after cooling, poured on ice water, which is subsequently filtered. The residue is extracted with ether to yield 65 g 4,6-dichloro-2-isopropyl-5-nitro-pyrimidine; m.p. 32°C.

d. 5 g of 4,6-dichloro-2-isopropyl-3-nitro-pyrimidine are dissolved in 100 ml of abs. ethanol, the solution is treated with 5 ml of triethylamine and 5.9 g of isopropylamine and stirred overnight. The reaction mixture is evaporated, the product then taken up in water, and extracted with ether, to yield 5.5 g of 2-isopropyl-4,6-bis(diisopropylamino)-5-nitro-pyrimidine; m.p. 45°C.

EXAMPLE 12 a. 4,72 g (0.02 mol) of 4,6-dichloro-2-isopropyl-5-nitro-pyrimidine are dissolved in 100 ml of abs. ethanol. At −30°C, 2 g (0.02 mol) of triethylamine and 0.9 g (0.02 mol) of ethylamine are added and the mixture is then stirred for 4 hours at −20°C and for 6 hours at 0°C. Subsequently the reaction mixture is concentrated to dryness and the product is taken up in water and extracted with ether, to yield 4.5 g of 2-isopropyl-4-ethylamino-5-nitro-6-chloro-pyrimidine; m.p. 50°C.

b. 0.02 mol of 4-ethylamino-6-chloro-2-isopropyl-5-nitro-pyrimidine is dissolved in 100 ml of abs. ethanol. The solution is treated with 0.05 mol of triethylamine and 0.05 mol of isopropylamine and the mixture is stirred overnight. The reaction mixture is then concentrated to dryness and the product is taken up in water and extracted with ether. The yield of 2-isopropyl-4-ethylamino-5-isopropylamino-5-nitro-pyrimidine is 90%; $n_D^{20} = 1.5660$.

EXAMPLE 13

5.25 g (0.02 mol) of 4,6-dichloro-5-nitro-2-trifluoro-methyl-pyrimidine (J.Org.Chem. 26 (1961), pp. 4504–8) are dissolved in 150 ml of abs. ethanol. The solution is treated with 5 ml of triethylamine (0.05 mol) and 4.5 g (0.1 mol) of ethylamine and the mixture is stirred overnight, then evaporated to dryness. The residue is taken up in ether and washed with water. The ethereal phase is dried and concentrated to yield 5.5 g of 4,6-bis-ethylamino-5-nitro-2-trifluoromethylpyrimidine; m.p. 60°–65°C.

EXAMPLE 14 a. 5.25 g (0.02 mol) of 4,6-dichloro-5-nitro-2-trifluoro-methyl-pyrimidine are dissolved in 100 ml of abs. ethanol and the solution is cooled to −30°C. At this temperature, 2.0 g (0.02 mol) of triethylamine and 0.9 g (0.2 mol) of ethylamine are added. The mixture is stirred first for 4 hours at −20°C to −30°C and then for 6 hours at 0°C. After it has been left to stand overnight at 20°C, the reaction mixture is concentrated to dryness. The residue is taken up in ether and the solution washed with water. The ethereal phase is dried and concentrated to yield 5.3 g of 4-ethylamino-6-chloro-5-nitro-2-trifluoromethyl-pyrimidine as a pale yellow oil; $n_D^{20} = 1.4985$.

b. 5.4 g (0.02 mol) of 4-ethylamino-6-chloro-5-nitro-2-trifluoromethyl-pyrimidine are dissolved in 100 ml of abs. ethanol. The solution is treated with 2.3 g of triethylamine (0.023 mol) and 1.7 g (0.023 mol) of 2-aminobutane and the mixture is stirred overnight. After the mixture has been evaporated, the product is taken up in water and extracted with ether to yield 4.5 g of 4-ethylamino-5-nitro-6-(2-butylamino)-2-trifluoromethyl-pyrimidine; $n_D^{20} = 1.5209$.

A number of starting materials and intermediates required for the manufacture of new end products of the formula Ia are also new compounds which have been manufactured in accordance with the methods described in the first sections of some Examples. A list of such new starting materials and intermediates is provided in the following table.

Starting materials and intermediates of the formula

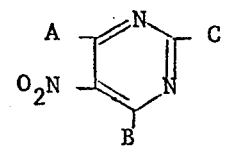

| A | B | C | | Physical Data |
|---|---|---|---|---|
| Cl | Cl | SCH₃ | m.p. | 58–60° |
| C₂H₅NH— | Cl | CH₃ | m.p. | 61–63° |
| 3-Pentyl-NH— | Cl | CH₃ | m.p. | 42–44° |
| Sec. C₄H₉—NH— | Cl | H | b.p. | 87°/0,001 Torr |
| i-C₃H₇—NH | Cl | Cl | m.p. | 72–74° |

I claim:

1. A 5-nitropyrimidine compound of the formula Ia

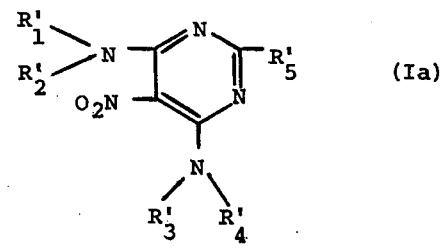

wherein $R'_1$ represents alkyl with 1 to 6 carbon atoms, alkenyl with at most 5 carbon atoms, cycloalkyl with 3 to 6 carbon atoms, hydroxyalkyl with 1 to 6 carbon atoms, or cyanoalkyl with 1 to 6 carbon atoms in the alkyl group, $R'_2$ and $R'_3$ each independently represents hydrogen or alkyl with 1 to 6 carbon atoms, $R'_4$ represents alkyl with 2 to 6 carbon atoms or cycloalkyl with 3 to 6 carbon atoms, $R'_5$ represents alkyl with 1 to 4 carbon atoms or trihalomethyl.

2. A nitropyrimidine derivative according to claim 1, wherein $R'_5$ in the formula Ia represents alkyl with 1 to 4 carbon atoms, $R'_1$ and $R'_4$ represent cycloalkyl with 3 to 6 carbon atoms or alkyl with 2 to 6 carbon atoms, at least one of which is branched, and the substituted amino in 4- and 6-position are different from each other.

* * * * *